United States Patent [19]

Aoyagi

[11] 4,326,876
[45] Apr. 27, 1982

[54] 2-AMINOSUBSTITUTED-5-METHYLENE-THIAZOLE AND 3-AMINOSUBSTITUTED-1 METHYLENE-2,4-THIAZASPIRO[5.4]DECANE HERBICIDES

[75] Inventor: Edward I. Aoyagi, Petaluma, Calif.

[73] Assignee: Chevron Research Company, San Francisco, Calif.

[21] Appl. No.: 115,593

[22] Filed: Jan. 28, 1980

[51] Int. Cl.$^3$ .......................................... C07D 277/08
[52] U.S. Cl. ................................ 71/090; 548/190; 548/193; 548/195; 548/196; 548/147
[58] Field of Search ................ 548/193, 194, 195, 196, 548/100, 147; 71/90

[56] References Cited

U.S. PATENT DOCUMENTS

| 2,780,631 | 2/1957 | Rauer | 548/195 |
| 2,879,273 | 3/1959 | Asinger et al. | 71/90 |
| 3,775,425 | 11/1973 | Bosshard et al. | 71/90 |
| 3,862,165 | 1/1975 | Amann et al. | 548/196 |

FOREIGN PATENT DOCUMENTS 7110558 3/1968 Japan .

OTHER PUBLICATIONS

CA 81 13439 X (1974).
CA 79 66237 V (1973).

*Primary Examiner*—Nicholas S. Rizzo
*Attorney, Agent, or Firm*—D. A. Newell; T. G. DeJonghe; G. F. Swiss

[57] ABSTRACT

Compounds of the following formula have herbicidal activity:

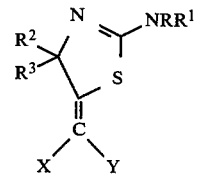

wherein X and Y are hydrogen or halo; $R^2$ and $R^3$ are alkyl or are joined to form $-(CH_2)_n-$, n=2 through 7; R is hydrogen, haloacetyl, alkyl, alkoxyalkyl or N-alkylcarbamoyl and $R^1$ is alkyl, alkenyl, alkynyl, cycloalkyl, polycycloalkyl, alkoxy-alkyl, cyanoalkyl or cyanoalkenyl; with the proviso that when R and $R^1$ are both alkyl, each contains at least 3 carbon atoms.

7 Claims, No Drawings

2-AMINOSUBSTITUTED-5-METHYLENE-THIAZOLE AND 3-AMINOSUBSTITUTED-1 METHYLENE-2,4-THIAZASPIRO[5.4]DECANE HERBICIDES

BACKGROUND OF THE INVENTION

Azerbaev et al. disclose 2-benzylamino-4,4-dialkyl-5-methylene-1,3-thiazolines in Chem. Abstr. 79:66237 v (1973).

Eloy et al disclose 2-alkylamino-5-methylene-thiazoles in Chem. Abstr. 81:13439x (1974).

SUMMARY OF THE INVENTION

The present invention relates to novel herbicidal compounds, compositions thereof and methods of their use. The present invention is based on the surprising observation that compounds of the formula (I) have a favorable herbicidal spectrum against weeds in post-emergent applications.

DESCRIPTION OF THE INVENTION

The present invention relates to compounds of the formula I:

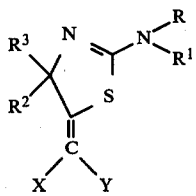

wherein X and Y are individually hydrogen or halogen;

$R^2$ and $R^3$ are individually alkyl of 1 to 3 carbon atoms or $R^2$ and $R^3$ are joined to form a cycloalkyl group of 3 to 8 carbon atoms;

R is hydrogen, haloacetyl, N-alkyl-carbamoyl of 2 to 10 carbon atoms, alkyl of 1 to 4 carbon atoms or alkoxyalkyl of 2 to 20 carbon atoms; and $R^1$ is alkyl of 1 to 20 carbon atoms, alkenyl or alkynyl of 3 to 20 carbon atoms, cycloalkyl or polycycloalkyl of 5 to 12 carbon atoms, alkoxyalkyl of 2 to 20 carbon atoms, cyanoalkyl or cyanoalkenyl of 3 to 20 carbon atoms; with the proviso that when R and $R^1$ are both alkyl groups as defined above, R and $R^1$ each contain at least 3 carbon atoms.

Representative $R^2$ and $R^3$ groups are methyl, ethyl, propyl or $R^2$ and $R^3$ are joined to form a cyclopentyl, cyclohexyl or cycloheptyl group. Preferably, $R^2$ and $R^3$ are joined to form a cyclohexyl group.

Representative R groups are hydrogen, methyl, ethyl, n-propyl, i-propyl, n-butyl, N-methyl carbamoyl, ethoxyethyl, methoxymethyl, chloroacetyl, bromoacetyl. Preferably R is hydrogen or N-methylcarbamoyl. Most preferably, R is hydrogen.

Representative $R^1$ groups are methyl, ethyl, n-propyl, t-butyl, sec-butyl, n-butyl, i-butyl, n-hexyl, n-octyl, 3-pentyl, n-pentyl, allyl, butenyl, propynyl, cyclopentyl, cyclohexyl, cyclohexylmethyl, 1-acetylenyl-cyclohex-1-yl, exonorborn-2-ane, 2-phenylethyl, p-chlorobenzyl, 4-phenylbutyl, 2-methoxyethyl, 3-methoxyprop-2-yl, ethoxyethyl, 2,2-dicyanoethylene and cyanoethyl. Preferably, $R^1$ is alkyl of 1 to 20 carbon atoms. Most preferably $R^1$ is alkyl of 1 to 6 carbon atoms.

The compounds of the invention may be made according to the following scheme:

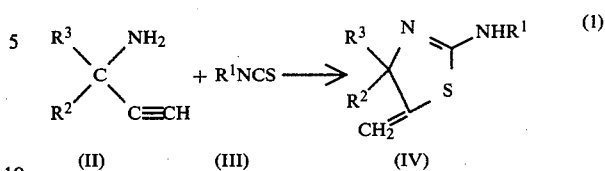

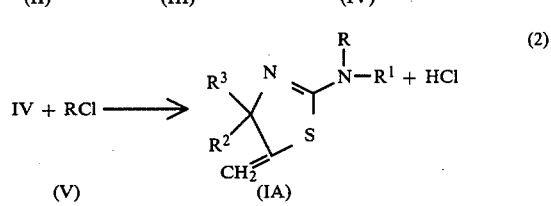

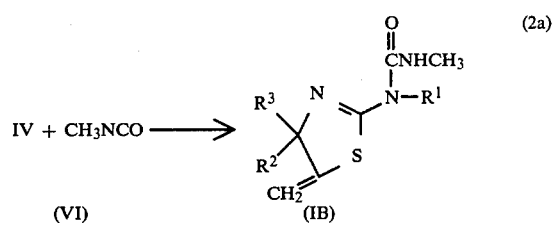

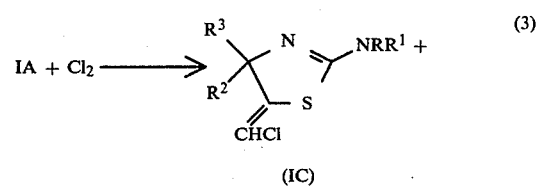

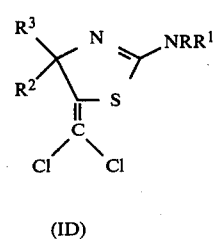

Reaction (1) is a conventional condensation and may be performed by reacting substantially equimolar portions of the amino propargyl compound (II) with the thiocyano compound (III) to form the cyclic intermediate (IV). The reaction may be conducted in a suitable inert solvent at 10° C. to 100° C., preferably at about 20° C.-30° C.

Reaction (2) is a conventional addition reaction which may be performed by reacting substantially equimolar amounts of the cyclic compound (IV) with the chloro compound in an inert diluent, preferably in presence of an organic base, such as, triethylamine, to serve as a scavenger for the evolved hydrogen chloride. The reaction may be carried out at room temperature.

The preferred method for making intermediate (IA) is according to reactions (1a) and (1b):

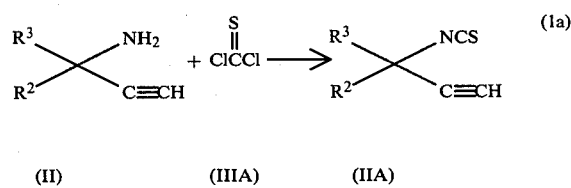

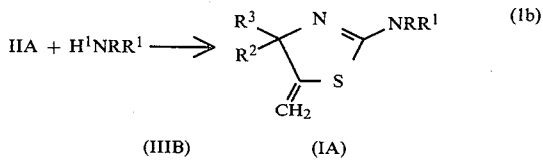

Reaction (1a) may be conducted in an inert organic diluent, preferably with water as a co-solvent. An organic base, such as a trialkylamine, may be added to scavenge the evolved hydrogen chloride. The reaction is exothermic and the mixture may be cooled to prevent boiling the solvent. The reaction is preferably carried out at room temperature employing a slight molar excess of thiophosgene (IIIA).

Reaction (1b) may be conducted with substantially equimolar amounts of (IIA) and amine (IIIB) in an inert organic diluent. The exothermic reaction may be conducted at 0°–100° C., preferably at 20°–40° C. If R is hydrogen, product (IA) from reaction (1b) can be further treated as in reaction (2a).

For compounds wherein R is N-methylcarbamoyl, reaction (2a) may be used. It is conducted in an inert solvent at room temperature in the presence of a base, such as triethylamine.

For compounds wherein X and Y are halogens, reaction (3) may be used. The mono- and dichloro compounds (IC) and (ID) are formed as a mixture by bubbling gaseous chlorine through a solution of (IA).

UTILITY

The compounds of the present invention are herbicidal in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broad-leaved weeds. Some may be selective with respect to the type of application and/or type of weed.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, atalpulgite and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application—i.e., sheltered areas such as greenhouses, as compared to exposed areas such as fields—as well as the desired type of control. Generally, for both pre- and post-emergent control, the herbicidal compounds of the invention are applied at rates of 0.2 to 60 kg/ha, and the preferred rate is in the range 0.5 to 40 kg/ha.

Pre-emergent herbicidal tests on representative compounds of the invention were made using the following method:

Pre-Emergent Test

An acetone solution of the test compound was prepared by mixing 750 mg of the compound, 220 mg of a nonionic surfactant and 25 ml of acetone. This solution was added to approximately 125 ml of water containing 156 mg of surfactant.

Seeds of the test vegetation were planted in a pot of soil and the test solution was sprayed uniformly onto the soil surface at a dose of 33 micrograms/cm$^2$ (3 lbs/acre). The pot was watered and placed in a greenhouse. The pot was watered intermittently and was observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table II.

Post-Emergent Test

The test compound was formulated in the same manner as described above for the pre-emergent test. The concentration of the test compound in this formulation was 5000 ppm. This formulation was uniformly sprayed on 2 similar pots of 24-day-old plants (approximately 15 to 25 plants per pot) at a dose of 33 mcg/cm$^2$ (3 lbs/acre). After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table II.

Example 1

Preparation of 3-(n-butyl-amino)-1-methylene-2,4-thiazaspiro[5.4]decane

To 1-ethynyl-1-amino-cyclohexane (50 g) in carbon tetrachloride (100 ml) was added dropwise 35 g n-butylthiocyanate. The mixture was stirred at room temperature for 3 days.

The mixture was stripped of solvent and filtered through a silica gel column in methylene chloride.

The product is reported as Compound 34 in Table I.

Example 2

Preparation of 3-(i-propylamino)-1-chloromethylene-2,4-thiazaspiro[5.4]decane 3-(i-Propylamino)-1-methylene-2,4-thiazaspiro [5.4]decane (A) was prepared as in Example 1 using i-propylthiocyanate.

Chlorine gas (4 g) was dissolved in 100 ml chloroform and added dropwise to product A (12.65 g). The mixture was stirred at room temperature for one hour, then chromatographed on a silica gel column. Elution by 50% $CH_2Cl_2$/Hexane and by $CH_2Cl_2$ yielded two products. The first product recovered was the dichloro product reported as Compound 59 in Table I. The second product was the title product, reported as Compound 58.

Example 3

Preparation of 3-(N-(N'-methylcarbamoyl)-ethylamino)-1-methylene-2,4-thiazaspiro5.4]decane 3-(ethylamino)-1-methylene-2,4-thiazaspiro [5.4]decane (B) was prepared as in Example 1.

Product B (7.2 g) was dissolved in 100 ml benzene and 2.9 g methyl isocyanate was added dropwise. A few drops of triethylamine were added and the mixture was stirred at room temperature for two hours. The mixture was stripped, stirred in hexane, filtered and stripped to yield a yellow oil. The product was crystallized in hexane, mp. 53–57, reported as Compound 39 in Table I.

Example 4

Preparation of 3-(sec-butylamino)-1-methylene-2,4-thiazaspiro[5.4]-decane

Thiophosgene (140 g) was dissolved in 250 ml methylene chloride and 250 ml water was added. To the two-phase system was added dropwise a solution of 1-ethynyl-1-amino-cyclohexane (123 g) and triethylamine (101 g) in 250 ml methylene chloride. The mixture was cooled to prevent refluxing. The mixture was stirred at room temperature for two hours, phase separated, and the organic phase was collected. This layer was dried ($MgSO_4$) and stripped, and the residue was dissolved in diethyl ether, filtered and stripped to yield a dark brown oil. A small portion of the oil was purified on a silica gel column (3×10 cm) with hexane elution to yield 1-isothiocyano-1-ethyl-cyclohexane (A), 5.9 g.

Compound A (10 g) was dissolved in 50 ml methylene chloride and sec-butylamine (4.5 g) was added dropwise. The exotherm caused refluxing and the stirring was continued overnight at room temperature after addition of 1.0 g excess sec-butylamine.

The solution was stripped, purified on a silica gel column (3×10 cm) with benzene and hexane elution. The eluates were stripped to yield the title product (9.5 g) as a reddish brown oil, reported as Compound 28 in Table I.

TABLE I

COMPOUNDS OF THE FORMULA

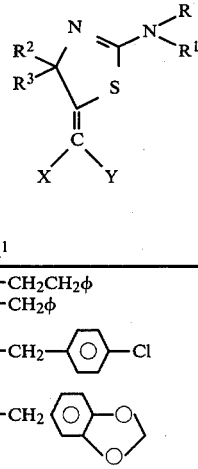

| No. | $R^2$ | $R^3$ | R | $R^1$ | X | Y | m.p., °C. | S Cal. | S Fd. | Cl Cal. | Cl Fd. |
|---|---|---|---|---|---|---|---|---|---|---|---|
| 1 | $-(CH_2)_5-$ | | H | $-CH_2CH_2\phi$ | H | H | Oil | 11.20 | 11.5 | | |
| 1A | $-(CH_2)_5-$ | | H | $-CH_2\phi$ | H | H | 56–58 | 11.77 | 10.9 | | |
| 2 | $-(CH_2)_5-$ | | H | $-CH_2-\langle\bigcirc\rangle-Cl$ | H | H | Oil | 10.45 | 10.7 | 11.56 | 11.7 |
| 3 | $-(CH_2)_5-$ | | H | $-CH_2\langle\bigcirc\rangle-O\rangle\!O$ | | | 82–84 | 10.13 | 10.6 | | |
| 4 | $-(CH_2)_5-$ | | H | $-(CH_2)_3\phi$ | H | H | Oil | 10.20 | 11.1 | | |
| 5 | $-(CH_2)_5-$ | | $CH_3$ | $-\overset{O}{\overset{\|}{C}}NHCH_3$ | H | H | 97–99 | 12.66 | 12.8 | | |
| 6 | $-(CH_2)_5-$ | | $-(CH_2)_3CH_3$ | $-CH=C(CN)_2$ | H | H | Oil | 10.20 | 10.1 | | |
| 7 | $-(CH_2)_5-$ | | H | $-CH_2-\langle\bigcirc\rangle$ | H | H | Oil | 11.60 | 12.1 | | |
| 8 | $-(CH_2)_5-$ | | H | $-CH(C_2H_5)_2$ | H | H | Oil | 12.70 | 13.6 | | |
| 9 | $-(CH_2)_5-$ | | H | $-\underset{CH_3}{\overset{}{C}H}CH_2CH(CH_3)_2$ | H | H | Oil | 12.04 | 13.3 | | |
| 10 | $-(CH_2)_5-$ | | H | $-\underset{CH_3}{\overset{}{C}H}-CH(CH_3)_2$ | H | H | Oil | 12.70 | 14.5 | | |
| 11 | $-(CH_2)_5-$ | | H | $-CH_2CH_2CH(CH_3)_2$ | H | H | Oil | 12.70 | 13.7 | | |
| 12 | $-(CH_2)_5-$ | | H | $-(CH_2)_4CH_3$ | H | H | Oil | 12.70 | 13.1 | | |

TABLE I-continued

COMPOUNDS OF THE FORMULA $$\begin{array}{c} R^2 \\ R^3 \end{array}\!\!-\!\!CH_2\!-\!\!\begin{array}{c} N \\ \| \\ C\!-\!\!N \end{array}\!\!\begin{array}{c} R \\ R^1 \end{array}$$

| No. | R² | R³ | R | R¹ | X | Y | m.p., °C. | S Cal. | S Fd. | Cl Cal. | Cl Fd. |
|---|---|---|---|---|---|---|---|---|---|---|---|
| 13 | ⫛CH₂⫚₅ | | H | —C(CH₃)₂CH₂CH₃ | H | H | Oil | 12.71 | 14.0 | | |
| 14 | ⫛CH₂⫚₅ | | H | —C(CH₃)₂CH₂C(CH₃)₃ | H | H | Oil | 10.89 | 11.3 | | |
| 15 | ⫛CH₂⫚₅ | | H | cyclopentyl | H | H | Oil | 12.81 | 12.6 | | |
| 16 | ⫛CH₂⫚₅ | | H | adamantyl | H | H | 112–114 | 10.13 | 10.2 | | |
| 17 | ⫛CH₂⫚₅ | | H | 1-ethynylcyclohexyl | H | H | Oil | 11.12 | 12.0 | | |
| 18 | ⫛CH₂⫚₅ | | H | norbornyl | H | H | Oil | 11.6 | 11.8 | | |
| 19 | ⫛CH₂⫚₅ | | H | ⫛CH₂⫚₁₁CH₃ | H | H | Oil | 9.15 | 8.7 | | |
| 20 | ⫛CH₂⫚₅ | | H | ⫛CH₂⫚₅CH₃ | H | H | Oil | 12.01 | 12.4 | | |
| 21 | ⫛CH₂⫚₅ | | H | ⫛CH₂⫚₇CH₃ | H | H | Oil | 10.89 | 11.1 | | |
| 22 | ⫛CH₂⫚₅ | | —CH₂CH₃ | ⫛CH₂⫚₃CH₃ | H | H | Oil | 12.04 | 13.2 | | |
| 23 | ⫛CH₂⫚₅ | | H | —CH₂CH(CH₃)₂ | H | H | Oil | 13.45 | 14.3 | | |
| 24 | ⫛CH₂⫚₅ | | —CH₂CH₂OCH₂CH₃ | —CH₂CH₂OCH₂CH₃ | H | H | Oil | 9.82 | 11.3 | | |
| 25 | ⫛CH₂⫚₅ | | H | —CH(CH₂)₅CH₃ \| CH₃ | H | H | Oil | 10.89 | 11.9 | | |
| 26 | ⫛CH₂⫚₅ | | H | —CHCH₂OCH₃ \| CH₃ | H | H | 64–67 | 12.61 | 13.1 | | |
| 27 | ⫛CH₂⫚₅ | | H | ⫛CH₂⫚₂OCH₃ | H | H | 58–61 | 13.34 | 14.3 | | |
| 28 | ⫛CH₂⫚₅ | | H | —CHCH₂CH₃ \| CH₃ | H | H | Oil | 13.45 | 14.2 | | |
| 29 | ⫛CH₂⫚₅ | | —C(=O)NHCH₃ | —CH₂CH₂CH₃ | H | H | 63–67 | 11.39 | 11.1 | | |
| 30 | ⫛CH₂⫚₅ | | ⫛CH₂⫚₂CH₃ | ⫛CH₂⫚₂CH₃ | H | H | Oil | 12.04 | 12.6 | | |
| 31 | ⫛CH₂⫚₅ | | —CH₃ | ⫛CH₂⫚₃CH₃ | H | H | Oil | 12.71 | 12.1 | | |
| 32 | ⫛CH₂⫚₅ | | H | —CH(CH₃)₂ | H | H | Oil | 14.30 | 13.7 | | |
| 33 | ⫛CH₂⫚₅ | | H | —C(CH₃)₃ | H | H | 57–58 | 13.46 | 13.8 | | |
| 34 | ⫛CH₂⫚₅ | | H | ⫛CH₂⫚₃CH₃ | H | H | Oil | 13.46 | 13.1 | | |
| 35 | ⫛CH₂⫚₅ | | H | —CH₂CH₂CH₃ | H | H | Oil | 14.29 | 14.1 | | |
| 36 | ⫛CH₂⫚₅ | | —C(=O)CH₂Cl | 4-methylcyclohexyl | H | H | Oil | 9.4 | 9.2 | 10.40 | 12.0 |
| 37 | ⫛CH₂⫚₅ | | —C(=O)CH₂Cl | —CH₂CH=CH₂ | H | H | Oil | 10.73 | 13.8 | 11.87 | 10.3 |
| 38 | ⫛CH₂⫚₅ | | H | CH₂CH=CH₂ | H | H | Oil | 14.4 | 16.2 | | |
| 39 | ⫛CH₂⫚₅ | | —C(=O)NHCH₃ | —C₂H₅ | H | H | 53–57 | 12.0 | 12.9 | | |
| 40 | ⫛CH₂⫚₅ | | H | —C₂H₅ | H | H | Oil | 15.25 | 14.8 | | |
| 41 | ⫛CH₂⫚₅ | | —C(=O)NHCH₃ | cyclohexyl | H | H | 81–84 | 9.98 | 10.2 | | |
| 42 | ⫛CH₂⫚₅ | | H | cyclohexyl | H | H | Oil | 12.13 | 12.13 | | |
| 43 | —C₂H₅ | —C₂H₅ | H | —C(CH₃)₃ | H | H | Oil | 14.17 | 14.4 | | |
| 44 | —CH₃ | —CH₃ | H | ⫛CH₂⫚₁₁CH₃ | H | H | 54–57 | 10.33 | 9.8 | | |
| 45 | —C₂H₅ | —C₂H₅ | H | ⫛CH₂⫚₃CH₃ | H | H | Oil | 14.17 | 14.7 | | |
| 46 | —C₂H₅ | —C₂H₅ | H | —CH(CH₃)₂ | H | H | Oil | 15.10 | 15.6 | | |
| 47 | —CH₃ | —CH₃ | H | ⫛CH₂⫚₅CH₃ | H | H | Oil | 13.34 | 14.3 | | |
| 48 | —CH₃ | —CH₃ | —C(=O)NHCH₃ | —CH₃ | H | H | Oil | 15.03 | 15.8 | | |

TABLE I-continued
COMPOUNDS OF THE FORMULA

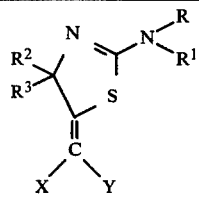

| No. | R² | R³ | R | R¹ | X | Y | m.p., °C. | S Cal. | S Fd. | Cl Cal. | Cl Fd. |
|---|---|---|---|---|---|---|---|---|---|---|---|
| 49 | —C₂H₅ | —C₂H₅ | O‖—CNHCH₃ | —CH₃ | H | H | Oil | 13.29 | 14.2 | | |
| 50 | —C₂H₅ | —C₂H₅ | —CNHCH₃ | —C₂H₅ | H | H | Oil | 14.11 | 15.2 | | |
| 51 | —CH₃ | —CH₃ | O‖—CNHCH₃ | ⌬ | H | H | 67–69 | 11.39 | 11.6 | | |
| 52 | —CH₃ | —CH₃ | H | ⌬ | H | H | 89–93 | 14.29 | 12.7 | | |
| 53 | ─(CH₂)₅─ | | H | ─(CH₂)₅CH₃ | Cl | H | Oil | 59.87¹ | 58.8¹ | 9.31² 8.37³ | 8.9² 8.26³ |
| 54 | ─(CH₂)₅─ | | H | ─(CH₂)₅CH₃ | Br | H | Oil | 52.16¹ | 50.53¹ | 8.11² 7.30³ | 7.53² 7.1³ |
| 55 | ─(CH₂)₅─ | | H | ─(CH₂)₅CH₃ | Cl | Cl | Oil | 53.72¹ | 54.11¹ | 8.36² 7.21³ | 7.96² 7.55³ |
| 56 | ─(CH₂)₅─ | | H | —C(CH₃)₃ | Cl | H | 104–108 | 57.22¹ | 57.35¹ | 10.27² 7.76³ | 10.27² 7.66³ |
| 57 | ─(CH₂)₅─ | | H | —C(CH₃)₃ | Cl | Cl | 60–64 | 50.81¹ | 50.39¹ | 9.12² 6.56³ | 8.92² 6.49³ |
| 58 | ─(CH₂)₅─ | | H | —CH(CH₃)₂ | Cl | H | Oil | 55.68¹ | 51.52¹ | 10.83² 7.40³ | 9.87² 6.98³ |
| 59 | ─(CH₂)₅─ | | H | —CH(CH₃)₂ | Cl | Cl | — | 49.14¹ | 52.51¹ | 9.55² 6.19³ | 10.06² 6.91³ |
| 60 | ─(CH₂)₅─ | | H | ─(CH₂)₅CH₃ | Cl | Cl | Oil | 50.81¹ | 50.96¹ | 9.12² 6.56³ | 9.34² 6.66³ |
| 61 | ─(CH₂)₅─ | | H | —CH(CH₃)₂ | Br | H | Oil | 47.52¹ | 49.87¹ | 9.24² 6.31³ | 8.74² 6.71³ |
| 62 | ─(CH₂)₅─ | | H | ─(CH₂)₅CH₃ | Br | H | Oil | 49.2¹ | 47.4¹ | 8.83² 6.67³ | 8.48² 6.54³ |
| 40A | ─(CH₂)₅─ | | H | —CH₃ | H | H | 77–8 | 16.34 | 16.2 | | |
| 40B | (1) | — | — | — | — | — | Oil | 15.25 | 15.5 | | |

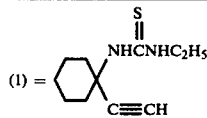

(1) = cyclohexyl with NHCNHC₂H₅ (C=S) and C≡CH substituents

¹Carbon
²Nitrogen
³Hydrogen

TABLE II
Herbicidal Efficacy Percent Control-Pre/Post

| No. | L | M | P | C | W | O |
|---|---|---|---|---|---|---|
| 1 | 0/70 | 0/100 | 0/25 | 0/55 | 0/30 | 0/40 |
| 1A | 0/80 | 25/— | 0/55 | 0/65 | 0/80 | 0/50 |
| 2 | 0/15 | 0/100 | 0/0 | 0/25 | 0/30 | 0/25 |
| 3 | 0/15 | 0/35 | 0/10 | 0/0 | 0/0 | 0/0 |
| 4 | 0/75 | 0/95 | 0/50 | 0/55 | 0/55 | 0/30 |
| 5 | 0/10 | 0/50 | 0/10 | 0/0 | 0/0 | 0/0 |
| 6 | 0/30 | 0/100 | 0/0 | 0/15 | 0/10 | 0/0 |
| 7 | 0/50 | 0/100 | 0/65 | 0/15 | 0/15 | 0/15 |
| 8 | 0/90 | 0/100 | 0/60 | 0/65 | 0/65 | 0/65 |
| 9 | 65/75 | 65/75 | 65/75 | 0/50 | 0/60 | 0/15 |
| 10 | 0/35 | 0/50 | 0/50 | 0/75 | 0/80 | 0/45 |
| 11 | 0/95 | 0/100 | 0/70 | 0/80 | 0/80 | 0/75 |
| 12 | 0/100 | 0/100 | 0/100 | 0/70 | 0/75 | 0/50 |
| 13 | 0/60 | 0/85 | 0/55 | 0/85 | 0/85 | 0/30 |
| 14 | 0/30 | 0/100 | 0/25 | 0/70 | 0/60 | 0/50 |
| 15 | 0/25 | 0/50 | 0/10 | 0/55 | 0/60 | 0/60 |
| 16 | 0/0 | 0/100 | 0/0 | 0/0 | 0/0 | 0/0 |
| 17 | 0/20 | 0/100 | 0/0 | 0/0 | 0/0 | 0/0 |
| 18 | 0/80 | 0/95 | 0/60 | 0/35 | 0/60 | 0/40 |
| 19 | 0/10 | 0/100 | 0/25 | 0/35 | 0/35 | 0/35 |
| 20 | 0/100 | 0/100 | 0/85 | 0/73 | 0/80 | 0/80 |
| 21 | —/98 | 0/100 | 0/60 | 0/80 | 0/75 | 0/60 |
| 22 | —/20 | 0/100 | 0/0 | 0/15 | 0/0 | 0/0 |
| 23 | —/85 | 0/98 | 0/25 | 0/65 | 0/75 | 0/70 |
| 24 | —/35 | 0/98 | 0/20 | 0/35 | 0/0 | 0/0 |
| 25 | —/92 | 0/88 | 0/92 | 0/72 | 0/85 | 0/82 |
| 26 | —80 | 0/— | 0/32 | 0/47 | 0/55 | 0/50 |
| 27 | —/60 | 0/— | 0/10 | 0/35 | 0/25 | 0/80 |
| 28 | —/95 | 0/— | 0/80 | 0/70 | 0/55 | 0/70 |
| 29 | 0/30 | 0/— | 0/50 | 0/0 | 0/0 | 0/0 |
| 30 | 0/25 | 0/— | 0/0 | 0/43 | 0/25 | 0/20 |
| 31 | 0/0 | 0/0 | 0/15 | 0/40 | 0/35 | 0/60 |
| 32 | 0/100 | 0/— | 0/15 | 0/96 | 0/93 | 0/97 |
| 33 | 0/30 | 0/— | 0/30 | 0/99 | 0/99 | 0/100 |
| 34 | 0/100 | 0/100 | 0/55 | 0/55 | 0/95 | 0/97 |
| 35 | 0/70 | 0/100 | 0/15 | 0/30 | 0/80 | 0/65 |
| 36 | 0/0 | 0/93 | 0/0 | 0/0 | 0/0 | 0/0 |
| 37 | 0/10 | 0/40 | 0/0 | 0/0 | 0/0 | 0/0 |
| 38 | 0/20 | 0/85 | 0/20 | 0/0 | 0/0 | 0/0 |
| 39 | 0/95 | 0/100 | 0/95 | 0/50 | 0/95 | 0/25 |

TABLE II-continued

Herbicidal Efficacy
Percent Control-Pre/Post

| No. | L | M | P | C | W | O |
|---|---|---|---|---|---|---|
| 40 | 0/25 | 0/100 | 0/40 | 0/30 | 0/50 | 0/55 |
| 40A | 0/5 | 0/35 | 0/0 | 0/0 | 0/0 | 0/0 |
| 40B | 0/85 | 0/100 | 0/65 | 0/40 | 0/70 | 0/55 |
| 41 | 0/25 | 0/80 | 0/10 | 0/0 | 0/0 | 0/0 |
| 42 | 0/70 | 0/95 | 0/25 | 0/50 | 0/40 | 0/25 |
| 43 | 0/0 | 0/60 | 0/0 | 0/0 | 0/0 | 0/0 |
| 44 | 0/55 | 0/85 | 0/65 | 0/10 | 0/20 | 0/15 |
| 45 | 0/40 | 0/100 | 0/25 | 0/35 | 0/35 | 0/25 |
| 46 | 0/0 | 0/85 | 0/0 | 0/0 | 0/0 | 0/0 |
| 47 | 0/90 | 0/95 | 0/90 | 0/30 | 0/60 | 0/55 |
| 48 | 97/40 | 97/60 | 77/30 | 80/0 | 90/0 | 95/0 |
| 49 | 0/25 | 0/20 | 0/20 | 0/0 | 0/0 | 0/0 |
| 50 | 80/75 | 93/— | 25/70 | 60/60 | 90/80 | 87/97 |
| 51 | 0/10 | 0/75 | 0/10 | 0/15 | 0/15 | 0/15 |
| 52 | 0/10 | 0/75 | 0/0 | 0/0 | 0/0 | 0/0 |
| 53 | 0/40 | 0/100 | 0/0 | 0/10 | 0/60 | 0/55 |
| 54 | 0/37 | 0/85 | 0/25 | 0/10 | 0/37 | 0/0 |
| 55 | 0/20 | 0/45 | 0/0 | 0/0 | 0/0 | 0/0 |
| 56 | 0/15 | 0/100 | 0/10 | 0/0 | 0/27 | 0/35 |
| 57 | 0/20 | 0/50 | 0/0 | 0/0 | 0/0 | 0/0 |
| 58 | 0/65 | 0/100 | 0/60 | 0/30 | 0/60 | 0/00 |
| 59 | 0/20 | 0/100 | 0/15 | 0/10 | 0/50 | 0/35 |
| 60 | 0/30 | 0/90 | 0/30 | 0/10 | 0/35 | 0/35 |
| 61 | 0/55 | 0/97 | 0/35 | 0/15 | 0/40 | 0/45 |
| 62 | 0/80 | 0/95 | 0/30 | 0/25 | 0/55 | 0/10 |

O = Wild Oats (*Avena fatua*)
W = Watergrass (*Echinochloa crusgalli*)
C = Crabgrass (*Digitaria Sanguinalis*)
M = Mustard (*Brassica arvensis*)
P = Pigweed (*Amaranthus retroflexus*)
L = Lambsquarter (*Chenopodium album*)

What is claimed is:

1. A compound of the formula

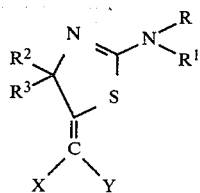

wherein X and Y are individually hydrogen or halogen; $R^2$ and $R^3$ are individually alkyl of 1 to 3 carbon atoms or $R^2$ and $R^3$ are joined to form a cycloalkyl group of 3 to 8 carbon atoms;

R is hydrogen, alkyl of 1 to 4 carbon atoms or alkoxyalkyl of 2 to 20 carbon atoms; and $R^1$ is alkyl of 1 to 20 carbon atoms, alkenyl or alkynyl of 3 to 20 carbon atoms, cycloalkyl or polycycloalkyl of 5 to 12 carbon atoms, alkoxyalkyl of 2 to 20 carbon atoms, cyanoalkyl or cyanoalkenyl of 3 to 20 carbon atoms; with the proviso that when R and $R^1$ are both alkyl groups as defined above, R and $R^1$ each contain at least 3 carbon atoms.

2. A compound according to claim 1 wherein $R^2$ and $R^3$ are joined to form a cyclopentyl, cyclohexyl or cycloheptyl ring.

3. A compound according to claim 2 wherein $R^2$ and $R^3$ form a cyclohexyl ring.

4. A compound according to claim 3 wherein X and Y are hydrogen.

5. A compound according to claim 4 wherein $R^1$ is alkyl of 2 to 20 carbon atoms.

6. The compound according to claim 5 wherein R is hydrogen and $R^1$ is iso-butyl.

7. An herbicidal composition comprising a biologically inert carrier and an herbicidally effective amount of a compound of the formula defined in claim 1.

* * * * *